United States Patent [19]

Stern et al.

[11] Patent Number: 5,380,946
[45] Date of Patent: Jan. 10, 1995

[54] PROCESS FOR PREPARING P-NITROAROMATIC AMIDES AND PRODUCTS THEREOF

[75] Inventors: Michael K. Stern, University City; Brian K. M. Cheng, St. Charles, both of Mo.

[73] Assignee: Monsanto Company, St. Louis, Mo.

[21] Appl. No.: 99,973

[22] Filed: Jul. 30, 1993

[51] Int. Cl.$^6$ .................. C07C 231/06; C07C 233/66
[52] U.S. Cl. .................................... 564/124; 564/126; 564/130; 564/164; 564/166; 564/337; 564/343; 564/397; 564/409; 564/416; 562/44; 562/47; 562/435; 562/564
[58] Field of Search ............... 564/124, 126, 166, 129, 564/130, 16.4; 562/44, 47, 435, 564; 558/412, 413, 436

[56] References Cited

U.S. PATENT DOCUMENTS

| | | |
|---|---|---|
| 3,270,026 | 8/1966 | Berger et al. ................ 564/166 |
| 3,414,616 | 12/1968 | Summers et al. ............. 260/566 |
| 3,530,153 | 9/1970 | Potts et al. ................... 564/126 |
| 3,825,596 | 7/1974 | Naito et al. .................. 564/124 |
| 3,847,990 | 11/1974 | Blahak ......................... 260/576 |
| 4,122,118 | 10/1978 | George et al. ................ 260/576 |
| 4,140,716 | 2/1979 | Maender et al. ........... 260/562 R |
| 4,155,936 | 5/1979 | Sturm .......................... 260/576 |
| 4,178,315 | 12/1979 | Zengel et al. ................. 260/647 |
| 4,187,248 | 2/1980 | Merten et al. ................ 260/576 |
| 4,187,249 | 2/1980 | Maender et al. ............. 260/576 |
| 4,196,146 | 4/1980 | Merten et al. ................ 260/576 |
| 4,209,463 | 6/1980 | Maender et al. ............. 260/576 |
| 4,404,401 | 9/1983 | Zengel et al. ................. 564/416 |
| 4,463,191 | 7/1984 | D'Sidocky et al. ........... 564/398 |
| 4,479,008 | 10/1984 | Batorewicz et al. .......... 564/433 |
| 4,518,803 | 5/1985 | Batorewicz et al. .......... 564/410 |
| 4,614,817 | 9/1986 | Maender et al. ............. 564/406 |
| 4,670,595 | 6/1987 | Podder et al. ................ 564/406 |
| 4,683,332 | 7/1987 | Sturm .......................... 564/414 |
| 4,760,186 | 7/1988 | Solodar ........................ 564/435 |
| 4,801,748 | 1/1989 | Murahashi et al. .......... 564/124 |
| 4,900,868 | 2/1990 | Merten et al. ................ 564/398 |

FOREIGN PATENT DOCUMENTS 293999 12/1988 European Pat. Off.
453885 10/1991 European Pat. Off.

OTHER PUBLICATIONS

Cannon et al., *J. Org. Chem.*, vol. 18, pp. 516–520, 1953.
Elmorsy et al., *Tetrahedron Lett.*, 32(15), pp. 1825–1826, 1991.
Martinez, A. G. et al., *Tetrahedron Lett.*, 30(5), pp. 581–582, 1989.
Serial No. 07/888,999 Pending Stern et al.

(List continued on next page.)

*Primary Examiner*—Shailendra Kumar
*Attorney, Agent, or Firm*—Kenneth D. Goetz; Paul L. Passley; James C. Bolding

[57] ABSTRACT

A process for preparing p-nitroaromatic amides is provided which comprises contacting a nitrile, nitrobenzene, a suitable base and water in the presence of a suitable solvent system to form a mixture, and reacting the mixture at a suitable temperature in a confined reaction zone in the presence of a controlled amount of protic material. The p-nitroaromatic amides of the invention can be reduced to p-aminoaromatic amides. In one embodiment, the p-aminoaromatic amide is further reacted with ammonia under conditions which produce the corresponding p-aminoaromatic amine and the amide corresponding to the nitrile starting material or with water in the presence of a suitable basic or acidic catalyst under conditions which produce the corresponding p-aminoaromatic amine and the acid or salt thereof corresponding to the nitrile starting material. In another embodiment, the p-aminoaromatic amine is reductively alkylated to produce alkylated p-aminoaromatic amine. The p-nitroaromatic amide can be reacted with ammonia under conditions which produce the corresponding p-aminoaromatic amine and the amide corresponding to the nitrile starting material or with water in the presence of a suitable basic or acidic catalyst under conditions which produce the corresponding p-aminoaromatic amine and the acid or salt thereof corresponding to the nitrile starting material. In one embodiment, the p-nitroaromatic amine is reduced to produce p-aminoaromatic amine. In another embodiment, the p-aminoaromatic amine is reductively alkylated to produce alkylated p-aminoaromatic amine. In another embodiment, the p-nitroaromatic amine is reductively alkylated to produce p-aminoaromatic amine.

15 Claims, No Drawings

OTHER PUBLICATIONS

Serial No. 08/045,309 Pending Stern et al.

Faust, G., *J. Prakt. Chem.,* 6, pp. 14–17 (1958).

Ayyangar, N. R. et al., "A Novel Reaction of Acetanilide with Nitrobenzene in DMSO—An Unusual Solvent Assisted Regioselective Aromatic Nucleophilic Substitution", *Tetrahedron Letters,* vol. 31, No. 22, pp. 3217–20 (1990).

Wohl, A., "Toward the Knowledge of the Reaction Between Nitrobenzene and Aniline in the Presence of Alkali", *Chemische Berichte,* 36, pp. 4135–38 (1903).

Wohl, A. and Aue, W., *Chemische Berichte,* 34, pp. 2442–50 (1901).

Banerjee, A. A. and Mukesh D., "Heterogeneous Catalytic Transfer Hydrogenation of 4-Nitrodiphenylamine to p-Phenylenediamines", *J. Chem. Soc., Chem. Comm.,* 18, 1275–76 (1988).

Rylander, W. P., "Catalytic Hydrogenation in Organic Synthesis", Academic Press, pp. 113–14 and 299 (1979).

Jencks, W. P., *J. Am. Chem. Soc.,* 92, pp. 3201–3202 (1970).

PROCESS FOR PREPARING P-NITROAROMATIC AMIDES AND PRODUCTS THEREOF

BACKGROUND OF THE INVENTION

This invention relates to the production of p-nitroaromatic amides. In one aspect, this invention relates to the production of p-aminoaromatic amides. In another aspect, this invention relates to the production of p-nitroaromatic amines. In a further aspect, this invention relates to the production of p-aminoaromatic amines. In a still further aspect, this invention relates to the production of alkylated p-aminoaromatic amines.

Aromatic amide bonds are currently formed by the reaction of an amine with an acid chloride. Specifically, it is known to prepare p-nitroaromatic amides by the reaction of a nitroaromatic amine with an acid chloride. This process is disadvantageous in that the halide that is displaced is corrosive to the reactors and appears in the waste stream and must therefore be disposed of at considerable expense. Furthermore, the nitroaromatic amine is prepared by the reaction of halonitroaromatic, e.g., chloronitrobenzene, and ammonia and results in the same displacement of halide causing additional corrosion and waste disposal problems. Therefore, a non-halide route to substituted aromatic amides and specifically nitroaromatic amides and products thereof would provide significant advantages over current technology and result in a more efficient and economic commercial process.

The process of the invention is such a non-halide route to nitroaromatic amides and products thereof and therefore eliminates the expensive halide removal from the waste stream as well as corrosion problems caused by the halide.

SUMMARY OF THE INVENTION

It is an object of the invention to provide a process for producing p-nitroaromatic amides for use in the preparation of p-nitroaromatic amines, p-aminoaromatic amines, p-aminoaromatic amides and alkylated p-aminoaromatic amines. It is a further object of the invention to provide an efficient and economic process to produce p-nitroaromatic amides and products thereof that is commercially viable. It is a further object of the invention to provide a process for producing p-aminoaromatic amines for use as monomers in the production of polyamides or other polymer applications. It is a still further object of the invention to provide a process for producing alkylated p-aminoaromatic amines for use as antioxidants or antiozonants. It is a still further object of the invention to provide a process for producing p-nitroaromatic amines for use as intermediates to antioxidants.

According to the invention, a process for preparing p-nitroaromatic amides is provided which comprises contacting a nitrile, nitrobenzene, a suitable base and water in the presence of a suitable solvent system to form a mixture, and reacting the mixture at a suitable temperature in a confined reaction zone in the presence of a controlled amount of protic material.

Further, according to the invention, a process for preparing p-aminoaromatic amides is provided which comprises reducing the p-nitroaromatic amides prepared according to the invention. In one embodiment, the p-aminoaromatic amide is further reacted with ammonia under conditions which produce the corresponding p-aminoaromatic amine and the amide corresponding to the nitrile starting material. In another embodiment, the p-aminoaromatic amide is further reacted with water in the presence of a suitable basic or acidic catalyst under conditions which produce the corresponding p-aminoaromatic amine and the acid or salt thereof corresponding to the nitrile starting material. In a further embodiment, the p-aminoaromatic amine is reductively alkylated to produce alkylated p-aminoaromatic amine.

Further, according to the invention, the process for preparing p-nitroaromatic amines is provided which comprises reacting the p-nitroaromatic amide prepared according to the invention with ammonia under conditions which produce the corresponding p-nitroaromatic amine and the amide corresponding to the nitrile starting material or with water in the presence of a suitable basic or acidic catalyst under conditions which produce the corresponding p-nitroaromatic amine and the acid or salt thereof corresponding to the nitrile starting material. In one embodiment, the p-nitroaromatic amine is reduced to produce p-aminoaromatic amine. In another embodiment, the p-nitroaromatic amine is reductively alkylated to produce alkylated p-aminoaromatic amine. In another embodiment, the p-aminoaromatic amine is reductively alkylated to produce alkylated p-aminoaromatic amine.

DETAILED DESCRIPTION OF THE INVENTION

The invention relates to a process for preparing p-nitroaromatic amides comprising:

(a) contacting a nitrile, nitrobenzene, a suitable base and water in the presence of a suitable solvent system to form a mixture, and (b) reacting the mixture at a suitable temperature in a confined reaction zone in the presence of a controlled amount of protic material.

For producing p-aminoaromatic amides, the process of the invention further comprises:

(c) reducing the reaction product of (b) under conditions which produce p-aminoaromatic amides.

For producing p-aminoaromatic amines from p-aminoaromatic amides, the process of the invention further comprises:

(d) reacting the p-aminoaromatic amide with ammonia under conditions which produce the corresponding p-aminoaromatic amine and amide corresponding to the nitrile of (a).

Alternatively, for producing p-aminoaromatic amines from p-aminoaromatic amides, the process of the invention further comprises:

(d) reacting the p-aminoaromatic amide with water in the presence of a suitable basic or acidic catalyst under conditions which produce the corresponding p-aminoaromatic amine and the acid or salt thereof corresponding to the nitrile of (a).

For producing the alkylated p-aminoaromatic amine, the process of the invention further comprises:

(e) reductively alkylating the p-aminoaromatic amine.

For producing p-nitroaromatic amine, the process of the invention further comprises:

(c') reacting the reaction product of (b) with (i) ammonia or (ii) water in the presence of a suitable basic or acidic catalyst under conditions which produce the corresponding p-nitroaromatic amine and the amide corresponding to the nitrile of (a) or the acid or salt thereof corresponding to the nitrile of (a).

For producing alkylated p-aminoaromatic amine, the process of the invention further comprises:

(d') reductively alkylating the p-nitroaromatic amine.

For producing p-aminoaromatic amine, the process of the invention further comprises:

(d") reducing the p-nitroaromatic amine under conditions which produce the corresponding p-aminoaromatic amine.

For producing alkylated p-aminoaromatic amine, the process of the invention further comprises:

(e") reductively alkylating the p-aminoaromatic amine.

The p-nitroaromatic amide produced by the process of the invention can be in the form of the neutral compound, i.e., not in the form of a salt, and/or in the form of the salt of such p-nitroaromatic amide. The salt is produced in the reaction mixture from reaction of the p-nitroaromatic amide with the base. Thus, the reaction mixture produced in the process of the invention can include the p-nitroaromatic amide compound, or salts or mixtures thereof depending on the specific reaction conditions selected.

The molar ratio of nitrile to nitrobenzene can vary from a large excess of nitrile to a large excess of nitrobenzene. When nitrobenzene is used as the suitable solvent for the reaction, nitrobenzene is preferably present in a large excess relative to the nitrile. When the nitrile is used as the suitable solvent for the reaction, nitrile is preferably present in a large excess relative to the nitrobenzene. When nitrobenzene or nitrile is not used as the solvent for the reaction, the molar ratio of nitrile to nitrobenzene can vary over a wide range, but is preferably about 1:1.

Nitriles that can be employed according to the invention include aromatic nitriles, aliphatic nitriles, substituted aromatic nitrile derivatives, substituted aliphatic nitrile derivatives and dinitriles having the formula:

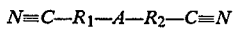

wherein $R_1$ and $R_2$ are independently selected from the group consisting of aromatic groups, aliphatic groups and a direct bond, and A is selected from the group consisting of

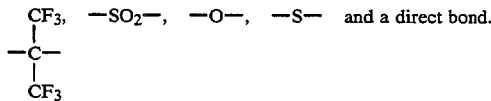

The aliphatic nitriles and substituted aliphatic nitrile derivatives that can be employed according to the invention are represented by the formula:

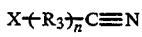

wherein n is 0 or 1, $R_3$ is selected from the group consisting of alkyl, arylalkyl, alkenyl, arylalkenyl, cycloalkyl and cycloalkenyl groups and X is selected from the group consisting of hydrogen, —$NO_2$, —$NH_2$, aryl groups, alkoxy groups, sulfonate groups, —$SO_3H$, —OH, —COH, —COOH, and alkyl, aryl, arylalkyl or alkylaryl groups containing at least one —$NH_2$ group. Sulfonate groups, as used herein, are the esters of sulfonic acids. Examples of sulfonates include, but are not limited to, alkyl sulfonates, aralkyl sulfonates, aryl sulfonates and the like. The preferred alkyl and alkoxy groups contain from 1 to about 6 carbon atoms. The preferred aryl, arylalkyl and alkylaryl groups contain from about 6 to about 18 carbon atoms.

Examples of aliphatic nitriles and substituted aliphatic nitrile derivatives include, but are not limited to, acetonitrile, n-valeronitrile, butyronitrile, isobutyronitrile, cyanamide, and mixtures thereof.

As used herein, the term "substituted aromatic nitrile derivatives" means aromatic nitriles containing one or more electron withdrawing or electron releasing substituents on the aromatic ring. Applicable substituents include, but are not limited to, halides, —$NO_2$, —$NH_2$, alkyl groups, alkoxy groups, sulfonate groups, —$SO_3H$, —OH, —COH, —COOH, and alkyl, aryl, arylalkyl or alkylaryl groups containing at least one —$NH_2$ group. Halides are selected from the group consisting of chloride, bromide and fluoride. The preferred alkyl and alkoxy groups contain from 1 to about 6 carbon atoms. The preferred aryl, arylalkyl and alkylaryl groups contain from about 6 to about 18 carbon atoms.

Examples of aromatic nitriles and substituted aromatic nitrile derivatives include, but are not limited to, benzonitrile, 4-methoxybenzonitrile, 4-chlorobenzonitrile, 4-nitrobenzonitrile, 4-aminobenzonitrile, o-tolunitrile, p-tolunitrile and mixtures thereof.

Dinitriles that can be employed according to the process of the invention include, but are not limited to, 1,4-dicyanobenzene, 1,4-dicyanobutane, 1,6-dicyanohexane, 2,6-dicyanotoluene, 1,2-dicyanocyclobutane, 1,2-dicyano-3,4,5,6-tetrafluorobenzene, 4,4'-dicyanobiphenyl and mixtures thereof.

The reaction for forming the p-nitroaromatic amide is carried out in a suitable solvent system. As used herein, the phase "suitable solvent system" means a polar aprotic solvent.

Suitable solvent systems include, but are not limited to, solvents such as, for example, nitrobenzene, dimethylsulfoxide, dimethylformamide, N-methyl-2-pyrrolidone, pyridine, N-methylaniline, chlorobenzene, tetrahydrofuran, 1,4-dioxane, tetraalkyl ammonium hydroxides or nitriles having a melting point below the reaction temperature, e.g., molten tetramethyl ammonium hydroxide and benzonitrile, and mixtures thereof. The currently preferred suitable solvents are nitrobenzene, dimethylsulfoxide, dimethylformamide and N-methyl-2-pyrrolidone. Most preferably, nitrobenzene is used in excess in the reaction as stated above, and the nitrobenzene in excess of the molar amount of nitrile serves as the solvent. As described in more detail below, solvent mixtures can be utilized wherein one or more of the suitable solvents and another solvent, such as a controlled amount of a protic solvent, are combined. Examples of protic solvent include, but are not limited to, methanol, water and mixtures thereof.

Suitable bases include, but are not limited to, organic and inorganic bases such as alkali metals, such as sodium metal, alkali metal hydrides, hydroxides and alkoxides, such as sodium hydride, lithium hydroxide, sodium hydroxide, cesium hydroxide, potassium hydroxide, potassium t-butoxide, and the like, including mixtures thereof. Other acceptable base materials include, but are not limited to, phase transfer catalysts in conjunction with a suitable base source such as tetrasubstituted ammonium hydroxides or halides wherein each substituent is independently selected from alkyl, aryl or arylalkyl groups wherein the alkyl, aryl and arylalkyl groups preferably have 1 to about 18 carbon atoms, including tetraalkyl ammonium hydroxides, e.g., tetramethyl ammonium hydroxide, tetraalkyl ammonium halides, e.g., tetrabutyl ammonium chloride, aryl, trialkyl ammonium hydroxides, e.g., phenyltrimethylammonium hydroxide, arylalkyl, trialkyl ammonium hydroxides, e.g., benzyltrimethyl ammonium hydroxide, alkyl substituted diammonium hydroxides, e.g., bis-dibutylethylhexamethylene diammonium hydroxide, and other combinations of phase transfer catalysts and suitable bases such as suitable bases in conjunction with aryl ammonium salts, crown ethers and the like, and amine bases such as lithium, bis(trimethysilyl) amide, and the like, including mixtures thereof. Preferred materials for use as bases are tetraalkylammonium hydroxides such as tetramethylammonium hydroxide or tetrabutylammonium hydroxide.

Preferably, the base and water are added to the nitrile to produce a mixture which is then combined with the nitrobenzene. Alternatively, the base and water can be added after the nitrile and nitrobenzene have been combined. Addition of materials can be above or below surface addition.

The amount of base employed according to the invention can be conveniently expressed in terms of the ratio of equivalents of suitable base to equivalents of nitrile. Broadly, the ratio of equivalents of base to equivalents of nitrile will be about 1:1 to about 10:1, preferably about 1:1 to about 4:1, and most preferably about 1:1 to about 2:1.

The reaction is conducted at a suitable temperature which can vary over a wide range. For example, the temperature can fall within a range of from about 5° C. to about 150° C., such as from about 15° C. to about 100° C., preferably from about 25° C. to about 90° C. A most preferred temperature for conducting the reaction of the invention is from about 60° C. to about 80° C.

Control of the amount of protic material present in the reaction is important. The amount of protic material employed according to the invention can be conveniently expressed in terms of a molar ratio based on the amount of base present at the beginning of the reaction which results in the formation of the p-nitroaromatic amide. Broadly, the molar ratio of protic material to base will be less than about 5:1, preferably less than about 3:1, more preferably less than about 2:1, and most preferably less than about 1:1. Thus, the present reaction could be conducted under anhydrous conditions. As used herein, the term "controlled amount" of protic material is an amount up to that which inhibits the formation of p-nitroaromatic amide. The upper limit for the amount of protic material present in the reaction varies with the solvent. In addition, the amount of protic material tolerated will vary with the type of base, amount of base, and base cation, used in the various solvent systems. However, it is within the skill of one in the art, utilizing the teachings of the present invention, to determine the specific upper limit of the amount of protic material for a specific solvent, type and amount of base, base cation and the like. The minimum amount of protic material necessary to maintain selectivity of the desired products will also depend upon the solvent, type and amount of base, base cation and the like, that is utilized and can also be determined by one skilled in the art.

Since the amount of protic material present in the reaction is important, it is possible to reduce the amount of protic material present as much as possible and then add back to the reaction the desired amount. Protic materials that can be utilized to add back to the reaction are known to those skilled in the art and include, but are not limited to, water, methanol and the like, and mixtures thereof. Methods for measuring the amount of protic material and for reducing the amount of protic material as much as possible are well known in the art. For example, the amount of water present in certain reagents can be determined by utilizing a Karl-Fischer apparatus, and the amount of water can be reduced through distillation and/or drying under reduced pressure, drying in the presence of $P_2O_5$ and other agents, azeotropic distillation utilizing, for example, xylene, and the like, including combinations thereof.

In one embodiment for controlling the amount of protic material during the reaction to form the p-nitroaromatic amide, a desiccant is added so as to be present during the reaction. For example, when the protic material is water, the desiccant removes water present during the reaction and results in higher conversion of nitrobenzene and yields of p-nitroaromatic amide. As used herein, desiccant is a compound present during the reaction in addition to the suitable base used. Examples of suitable desiccants include, but are not limited to, anhydrous sodium sulfate, molecular sieves, such as types 4A, 5A, and 13X available from the Union Carbide Corporation, calcium chloride, tetramethylammonium hydroxide dihydrate, anhydrous bases such as KOH and NaOH, and activated alumina. When the nitrile is used in excess in relation to the nitrobenzene, such as when the nitrile serves as the suitable solvent, the nitrile can serve as the desiccant.

In another embodiment for controlling the amount of protic material during the reaction to form the p-nitroaromatic amide, protic material is continuously removed from the reaction mixture by distillation. If the protic material present forms an azeotrope with one of the compounds in the reaction mixture, the protic material can be removed by continuous azeotropic distillation of protic material utilizing the azeotrope.

The reaction can be conducted under aerobic or anaerobic conditions. Under aerobic conditions, the reaction is conducted essentially as described above in the reaction zone which is exposed to oxygen, usually by exposure to air. Under aerobic conditions, the pressure at which the reaction is conducted can vary and the optimal pressure, as well as the optimal combination of pressure and temperature, are easily determined by one skilled in the art. For example, the reaction can be conducted at room temperature and at a pressure ranging from about 0 psig (0 kg/cm$^2$) to about 250 psig (17.6 kg/cm$^2$, such as from about 14 psig (1 kg/cm$^2$) to about 150 psig (10.5 kg/cm$^2$). Under anaerobic conditions, the reaction can be conducted at atmospheric pressure or reduced or elevated pressures, in the presence of an inert gas such as, for example, nitrogen or argon. Optimal conditions for a particular set of reaction parameters, such as temperature, base, solvent and the like, are easily determined by one skilled in the art utilizing the teaching of the present invention. It is currently preferred to conduct the reaction under aerobic conditions because formation of by-product azoxybenzene can be eliminated.

The p-nitroaromatic amides and/or their salts can be reduced to p-aminoaromatic amides. The neutral compounds can be generated from the salts utilizing water and/or an acid. Alternatively, the salts can be reduced. In another embodiment of the invention, p- nitroaromatic amine can be reduced to p-aminoaromatic amine. These reductions can be carried out by any of many known reductive processes, such as using a hydride source, e.g., sodium borohydride in conjunction with palladium- or platinum-on-carbon catalysts. Preferably, this reduction is conducted by a catalytic reduction wherein hydrogenation is effected under hydrogen pressure in the presence of platinum- or palladium-on-carbon, nickel, and the like. This hydrogenation process is described in detail in "Catalytic Hydrogenation in Organic Synthesis", P. N. Rylander Academic Press, New York, page 299 (1979), which is incorporated by reference herein. The hydrogenation can be conducted in a variety of solvents including, but not limited to, toluene, xylene, aniline, ethanol, dimethylsulfoxide, water and mixtures thereof. Preferably, the hydrogenation is conducted utilizing a platinum-on-carbon or palladium-on-carbon catalyst in a suitable solvent such as, for example, either ethanol, aniline, or dimethylsulfoxide, mixtures thereof, or mixtures which include water as the solvent and a hydrogen pressure of from 100 psig (7 kg/cm$^2$) H$_2$ to about 340 psig (23.9 kg/cm$^2$) H$_2$ at a temperature of about 80° C.

Aminolysis of p-nitroaromatic amide and p-aminoaromatic amide can be conducted by reacting p-nitroaromatic amide or p-aminoaromatic amide with ammonia to produce the corresponding p-nitroaromatic amine or p-aminoaromatic amine, respectively, and the amide corresponding to the nitrile starting material. See for example, Jencks, W. P., *J. Am. Chem. Soc.*, Vol. 92, pp. 3201-3202 (1970). The ammonia can be utilized in the aminolysis reaction as either ammonia or a mixture of ammonia and ammonium hydroxide. If ammonium hydroxide is present, the reaction will produce the acid corresponding to the nitrile starting material in addition to the amide corresponding to the nitrile starting material. Preferably, p-nitroaromatic amide or p-aminoaromatic amide is reacted with ammonia in the presence of a solvent, e.g., methanol.

Hydrolysis of p-nitroaromatic amide and p-aminoaromatic amide can be conducted by reacting p-nitroaromatic amide or p-aminoaromatic amide with water in the presence of a suitable basic or acidic catalyst to produce the corresponding p-nitroaromatic amine or p-aminoaromatic amine, respectively, and the acid or salt thereof corresponding to the nitrile starting material. Examples of suitable basic catalysts include, but are not limited to, alkali metal hydroxides, alkaline earth metal hydroxides, alkali metal alkoxides, tetraalkylammonium hydroxides, ammonium hydroxide, and the like, and mixtures thereof. Examples of suitable acidic catalysts include, but are not limited to, sulfuric acid, hydrochloric acid, nitric acid, phosphoric acid, and the like, and mixtures thereof. It is currently preferred to use a basic catalyst since selected suitable bases used in the preparation of p-nitroaromatic amides may also be utilized as the basic catalyst in the hydrolysis reaction. The temperature of the hydrolysis reaction will generally be in the range of about 60° C. to about 120° C.

Reductive alkylation of p-aminoaromatic amine to produce anti-oxidants or antiozonants can be conducted by any one of several well-known methods. See, for example, U.S. Pat. No. 4,900,868. Preferably, p-aminoaromatic amine and a suitable ketone or aldehyde are reacted in the presence of hydrogen and platinum-on-carbon as catalysts. Suitable ketones include, but are not limited to, methylisobutyl ketone (MIBK), acetone, methylisoamyl ketone and 2-octanone. It should be noted that reduction of p-nitroaromatic amines and alkylation of the reduced material can be conducted in the same reaction vessel utilizing the ketone as a solvent. See, for example, U.S. Pat. No. 3,414,616, U.S. Pat. No. 4,463,191, and Bannerjee et al, *J. Chem. Soc. Chem. Comm.*, 18, pp 275-76 (1988).

Contemplated equivalents of the reactants and reagents set forth above are reactants and reagents otherwise corresponding thereto and having the same general properties wherein one or more of the various groups, e.g., —NO$_2$ are simple variations. In addition, where a substituent is designated as, or can be, a hydrogen, the exact chemical nature of a substituent which is other than hydrogen at that position is not critical so long as it does not adversely affect the overall activity and/or synthesis procedure.

The chemical reactions described above are generally disclosed in terms of their broadest application to the process of this invention. Occasionally, the reaction conditions may not be applicable as specifically described to each reactant and reagent within the disclosed scope. For example, certain suitable bases may not be as soluble in one solvent as they are in other solvents. The reactants and reagents for which this occurs will be readily recognized by those skilled in the art. In all such cases, either the reactions can be successfully performed by conventional modifications known to those skilled in the art, e.g., by appropriate adjustments in temperature, pressure and the like, by changing to alternative conventional reagents such as other solvents or other bases, by routine modification of reaction conditions, and the like, or other reactions disclosed herein or otherwise conventional, will be applicable to the process of this invention. In all preparative methods, all starting materials are known or are readily preparable from known starting materials.

EXAMPLES

Materials and Methods

Nitriles and nitrobenzene were reagent grade and were used without further purification. Solvents were purchased from Aldrich Chemical and were anhydrous grade. The tetramethylammonium hydroxide was purchased as the pentahydrate and dried in a desiccator over P$_2$O$_5$ under vacuum for several days before use. Titration of the resulting solid showed the dried material to be the dihydrate. Unless indicated otherwise, all yields were determined by HPLC according to the following method. HPLC Analysis Method:

A Waters 600 series HPLC equipped with a Vydac 201HS54 (4.6 ×250 mm) column and UV detection at 254 nm was used to monitor all reactions. The external standard method was utilized in all the analyses. Authentic samples of products to be used as standards were prepared by known literature methods.

| | Elution Gradient | |
|---|---|---|
| Time (Min.) | % Solvent A (Water) | % Solvent B (40% Methanol in ACN) |
| 0 | 75 | 25 |
| 35 | 20 | 80 |
| 40 | 0 | 100 |
| 45 | 0 | 100 |
| 46 | 75 | 25 |
| 55 | 75 | 25 |

EXAMPLE 1

This example illustrates the preparation of N-(4-nitrophenyl)-benzamide by the reaction of benzonitrile and nitrobenzene in the presence of air.

A solution containing 10 g of nitrobenzene, 1.27 g of tetramethylammonium hydroxide dihydrate and 1 g of benzonitrile was stirred at 60° C. with air bubbled into the solution via a syringe needle for 1 hour. Analysis of a sample of the reaction product by HPLC revealed N-(4-nitrophenyl)-benzamide was produced in 45% yield based on the tetramethylammonium hydroxide. No azoxybenzene was detected in the reaction product.

EXAMPLE 2

This example illustrates the preparation of N-(4-nitrophenyl)-benzamide by the reaction of benzonitrile and nitrobenzene under anaerobic conditions.

A solution containing 10 g of nitrobenzene, 1.27 g of tetramethylammonium hydroxide dihydrate and 1 g of benzonitrile was stirred at 60° C. with nitrogen bubbled into the solution via a syringe needle for 1 hour. Analysis of a sample of the reaction product by HPLC revealed N-(4-nitrophenyl)-benzamide was produced in 45% yield and azoxybenzene was generated in 22% yield based on tetramethylammonium hydroxide.

Example 3

This example illustrates the effect of water on the production of N-(4-nitrophenyl)-benzamide in the reaction of benzonitrile and nitrobenzene.

A) A solution of 1.27 g of tetramethylammonium hydroxide dihydrate, 156 mg of biphenyl (as internal standard) and 10 ml of nitrobenzene was stirred in a 100 ml 3-neck round bottom flask equipped with a drying tube. Benzonitrile (1 mL) was added and stirred at 60° C. in air. After the solution was stirred for 3 hours, an aliquot was sampled for RP-HPLC analysis. The yield of N-(4-nitrophenyl)-benzamide was 17% based on tetramethylammonium hydroxide charged.

B) A solution of 1.8 g of tetramethylammonium hydroxide pentahydrate, 160 mg of biphenyl (as internal standard) and 10 ml of nitrobenzene was stirred in a 100 ml 3-neck round bottom flask equipped with a drying tube. Benzonitrile (1 mL) was added and stirred at 60° C. in air. After the solution was stirred for 3 hours, an aliquot was sampled for RP-HPLC analysis. The yield of N-(4-nitrophenyl)-benzamide was calculated to be 0.91% based on tetramethylammonium hydroxide charged.

What is claimed is:

1. A process for preparing p-nitroaromatic amides comprising:
   (a) contacting a nitrile, nitrobenzene, a suitable base and water in the presence of a suitable solvent system to form a mixture, and
   (b) reacting said mixture at a suitable temperature in a confined reaction zone in the presence of a controlled amount of protic material.

2. The process of claim 1 wherein said nitrile is selected from the group consisting of aromatic nitriles, aliphatic nitriles, substituted aromatic nitrile derivatives, substituted aliphatic nitrile derivatives and dinitriles having the formula:

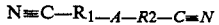

wherein $R_1$ and $R_2$ are independently selected from the group consisting of aromatic groups, aliphatic groups and a direct bond, and A is selected from the group consisting of

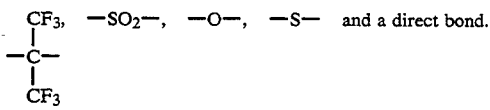

3. The process of claim 2 wherein said aliphatic nitriles and said substituted aliphatic nitrile derivatives are represented by the formula:

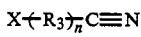

wherein n is 0 or 1, $R_3$ is selected from the group consisting of alkyl, arylalkyl, alkenyl, arylalkenyl, cycloalkyl and cycloalkenyl groups and X is selected from the group consisting of hydrogen, $-NO_2$, $-NH_2$, aryl groups, alkoxy groups, sulfonate groups, $-SO_3H$, $-OH$, $-COH$, $-COOH$, and alkyl, aryl, arylalkyl or alkylaryl groups containing at least one $-NH_2$ group.

4. The process of claim 2 wherein the substituent of said substituted aromatic nitrile derivatives is selected from the group consisting of halides, $-NO_2$, $-NH_2$, alkyl groups, alkoxy groups, sulfonate groups, $-SO_3H$, $-OH$, $-COOH$, $-COH$ and alkyl, aryl, arylalkyl or alkylaryl groups containing at least one $-NH_2$ group, wherein halides are selected from the group consisting of chloride, bromide and fluoride.

5. The process of claim 1 wherein said suitable solvent system includes a solvent selected from the group consisting of nitrobenzene, dimethylsulfoxide, dimethylformamide, N-methyl-2-pyrrolidone, pyridine, N-methylaniline, chlorobenzene, tetrahydrofuran, 1,4-dioxane, tetraalkyl ammonium hydroxide or nitriles having a melting point below the reaction temperature and mixtures thereof.

6. The process of claim 5 wherein said suitable solvent system includes a protic solvent.

7. The process of claim 1 wherein the molar ratio of said protic material to said suitable base is less than about 5:1 and the ratio of equivalents of said suitable base to equivalents of said nitrile is about 1:1 to about 10:1.

8. The process of claim 1 wherein said suitable temperature is from about 5° C. to about 150° C.

9. The process of claim 1 wherein said suitable base is selected from the group consisting of organic and inorganic bases.

10. The process of claim 9 wherein said organic and inorganic bases are selected from the group consisting of alkali metals, alkali metal hydrides, alkali metal hydroxides, alkali metal alkoxides, phase transfer catalyst in conjunction with a base source, amines, crown ethers in conjunction with a base source, alkyl magnesium halides, and mixtures thereof.

11. The process of claim 1 wherein said base is selected from the group consisting of an aryl ammonium, alkyl ammonium, aryl/alkyl ammonium and alkyl diammonium salt in conjunction with a base source.

12. The process of claim 1 wherein the reaction of step (b) is conducted under aerobic conditions.

13. The process of claim 1 wherein the reaction of step (b) is conducted under anaerobic conditions.

14. The process of claim 1 wherein a desiccant is present during Step (b) to control the amount of protic material present during the reaction.

15. The process of claim 1 wherein the amount of protic material of Step (b) is controlled by the continuous distillation of said protic material.